United States Patent [19]

Chu et al.

[11] Patent Number: 5,397,310
[45] Date of Patent: Mar. 14, 1995

[54] CATHETER INTRODUCER SHEATH ASSEMBLY

[75] Inventors: Michael S. H. Chu, Brookline; Yem Chin, Burlington; Fozan O. El-Nounou, Billerica; James B. Daigle, Worcester, all of Mass.; Andrew H. Cragg, Edina, Minn.

[73] Assignee: Boston Scientific Corporation, Watertown, Mass.

[21] Appl. No.: 24,789

[22] Filed: Mar. 1, 1993

Related U.S. Application Data

[63] Continuation of Ser. No. 775,046, Oct. 11, 1991.

[51] Int. Cl.$^6$ .............................................. A61M 5/178
[52] U.S. Cl. ..................................... 604/158; 604/167
[58] Field of Search ............... 604/158, 164, 167, 169, 604/256, 905, 246, 248; 251/4, 6

[56] References Cited

U.S. PATENT DOCUMENTS

| | | |
|---|---|---|
| 422,906 | 3/1890 | Booth . |
| 1,865,012 | 6/1932 | Jackson . |
| 2,667,324 | 1/1954 | Hansen ................................. 251/6 |
| 2,987,292 | 6/1961 | Teson . |
| 3,034,504 | 5/1962 | Winsor . |
| 3,197,173 | 7/1965 | Taubenheim . |
| 3,550,861 | 12/1970 | Teson . |
| 3,585,996 | 6/1971 | Reynolds . |
| 3,805,830 | 4/1974 | Smith . |
| 3,813,077 | 5/1974 | Kolic . |
| 3,861,641 | 1/1975 | Kolic . |
| 3,920,215 | 11/1975 | Knauf . |
| 4,016,879 | 4/1988 | Mellor . |
| 4,121,622 | 10/1978 | Forberg . |
| 4,243,034 | 1/1981 | Brandt ............................. 128/214.4 |

(List continued on next page.)

FOREIGN PATENT DOCUMENTS 745844 3/1956 United Kingdom .

OTHER PUBLICATIONS

Amplatz TractMaster System and Catheter-Medi-tech-Boston Scientific Corporation.
Torque Vise-Medi-Tech-Boston Scientific Corporation.
Tuohy-Borst Adapter With Side Port-Medi-Tech-Boston Scientific Corporation.
FloSwitch HP-Medi-Tech-Boston Scientific Corporation.
Quality Check Valves from Burron-Burron Medical Inc.

*Primary Examiner*—Gene Mancene
*Assistant Examiner*—Nicholas D. Lucchesi
*Attorney, Agent, or Firm*—Fish & Richardson

[57] ABSTRACT

A catheter introducer sheath assembly, for introduction into a body passage of a catheter containing a filter comprises a flexible introducer sheath joined to the distal end of a closure device forming a through-passage with a diameter sufficient to pass the catheter therethrough. The closure device has a resilient member in the through-passage and two rotatable body portions, one stationary with respect to the resilient member, and the other rotatable about the axis of the resilient member with an internal cam circumferentially spaced around the axis. A compression member positioned radially in an extending aperture makes contact with both the resilient member and the cam surface to vary the through-passage allowing the operator to manually control the passage of the device. The sheath assembly receives a cathetory guidewire that slides through and extends beyond the closure device and the sheath. In another aspect, the combination sheath assembly and closure device forms a catheter introducer kit constructed to receive a stabilizer and a catheter of sufficiently large diameter to house a vena cava filter, and to pass the filter through the closure device and sheath for placement in the body by means of a dilator attached to the end of the sheath to facilitate guiding the filter to the desired position for its release from the sheath. The closure device is adjustable to prevent any backflow of fluid such as blood from the assembly during the filter placement procedure.

23 Claims, 11 Drawing Sheets

U.S. PATENT DOCUMENTS

| | | |
|---|---|---|
| 4,314,555 | 2/1982 | Sagae . |
| 4,378,013 | 3/1983 | LeFevre . |
| 4,417,576 | 11/1983 | Baran . |
| 4,419,094 | 12/1983 | Patel ........................ 604/158 |
| 4,423,725 | 1/1984 | Baran . |
| 4,464,171 | 8/1984 | Garwin ...................... 604/53 |
| 4,490,003 | 12/1984 | Robinson . |
| 4,496,348 | 1/1985 | Genese et al. ............... 604/167 |
| 4,518,145 | 5/1985 | Keltz et al. .................. 251/5 |
| 4,540,411 | 9/1985 | Bodicky ....................... 604/169 |
| 4,697,785 | 10/1987 | Tuseth . |
| 4,714,460 | 12/1987 | Calderon ...................... 604/28 |
| 4,813,938 | 3/1989 | Raulerson .................... 604/167 |
| 4,834,719 | 5/1989 | Arenas . |
| 4,857,062 | 8/1989 | Russell ........................ 604/167 |
| 4,883,461 | 11/1989 | Sawyer ........................ 604/53 |
| 4,917,668 | 4/1990 | Haindt ......................... 604/167 |
| 4,960,412 | 10/1990 | Fink ............................ 604/167 |
| 4,978,341 | 12/1990 | Niederhauser ............... 604/167 |
| 5,009,391 | 4/1991 | Steigerwald ................. 604/167 |

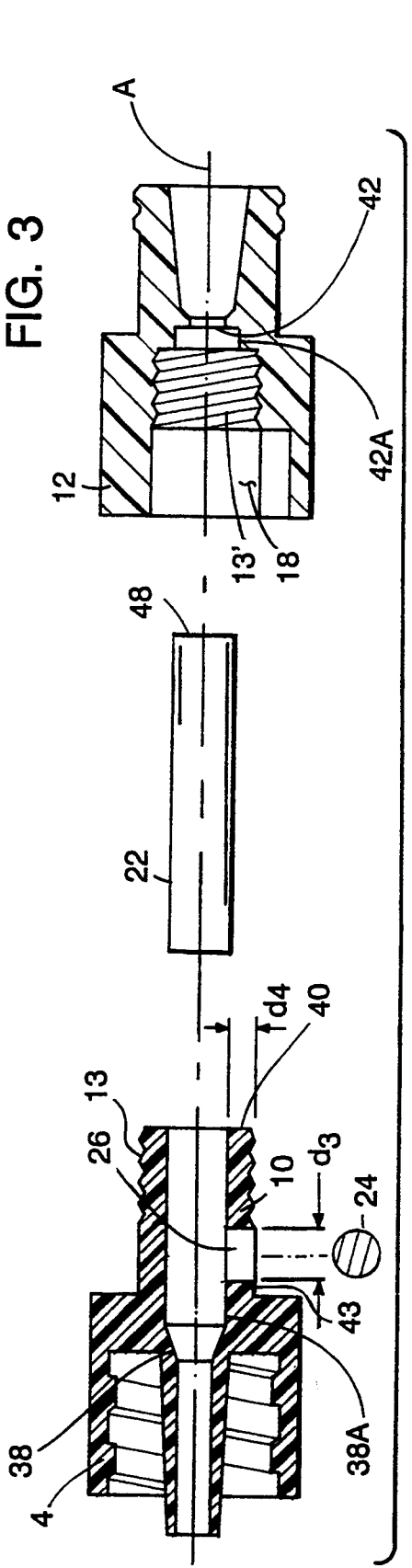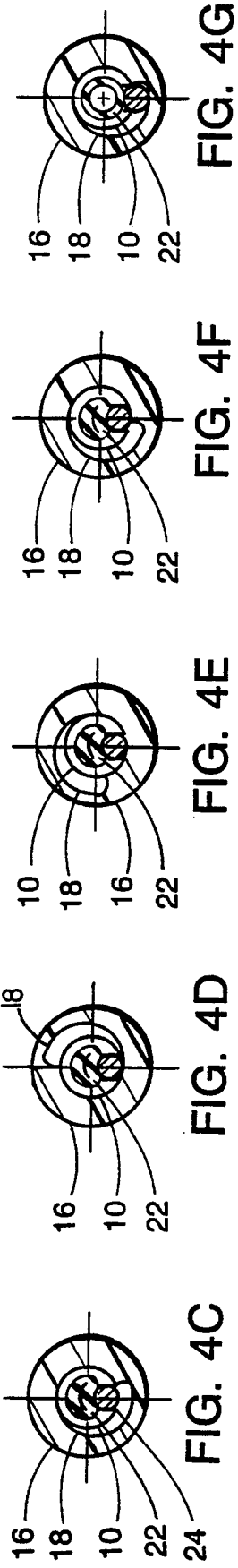

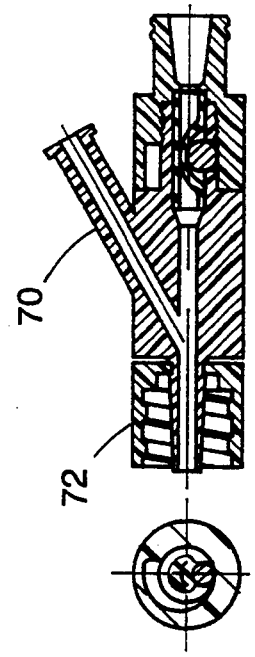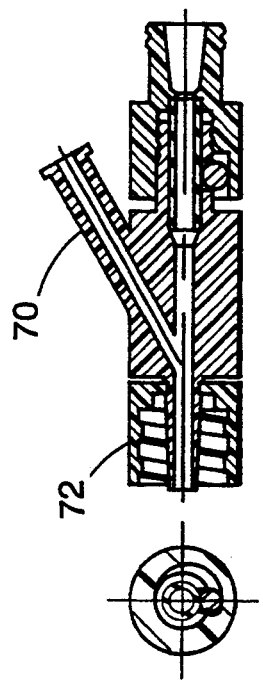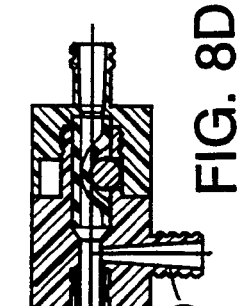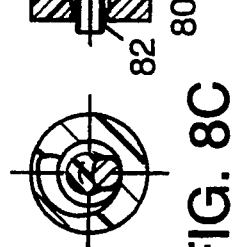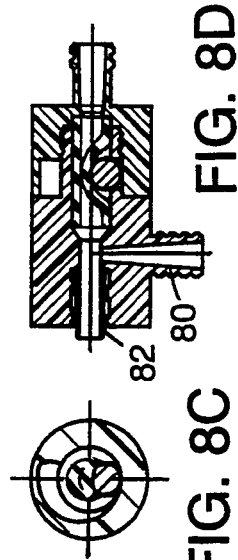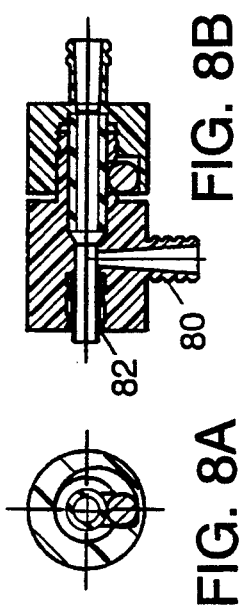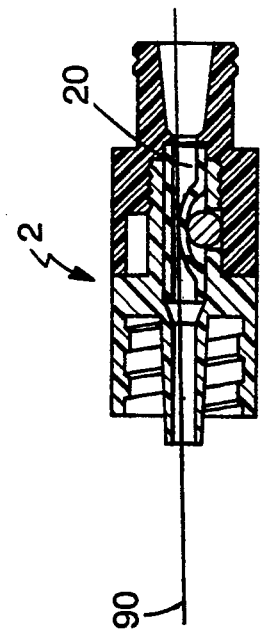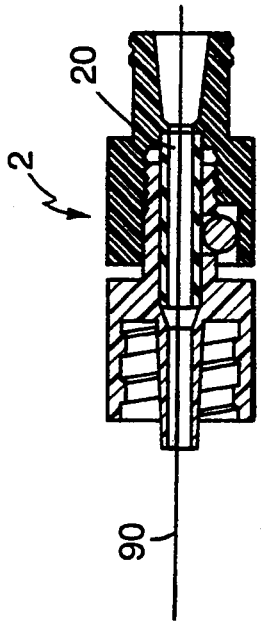

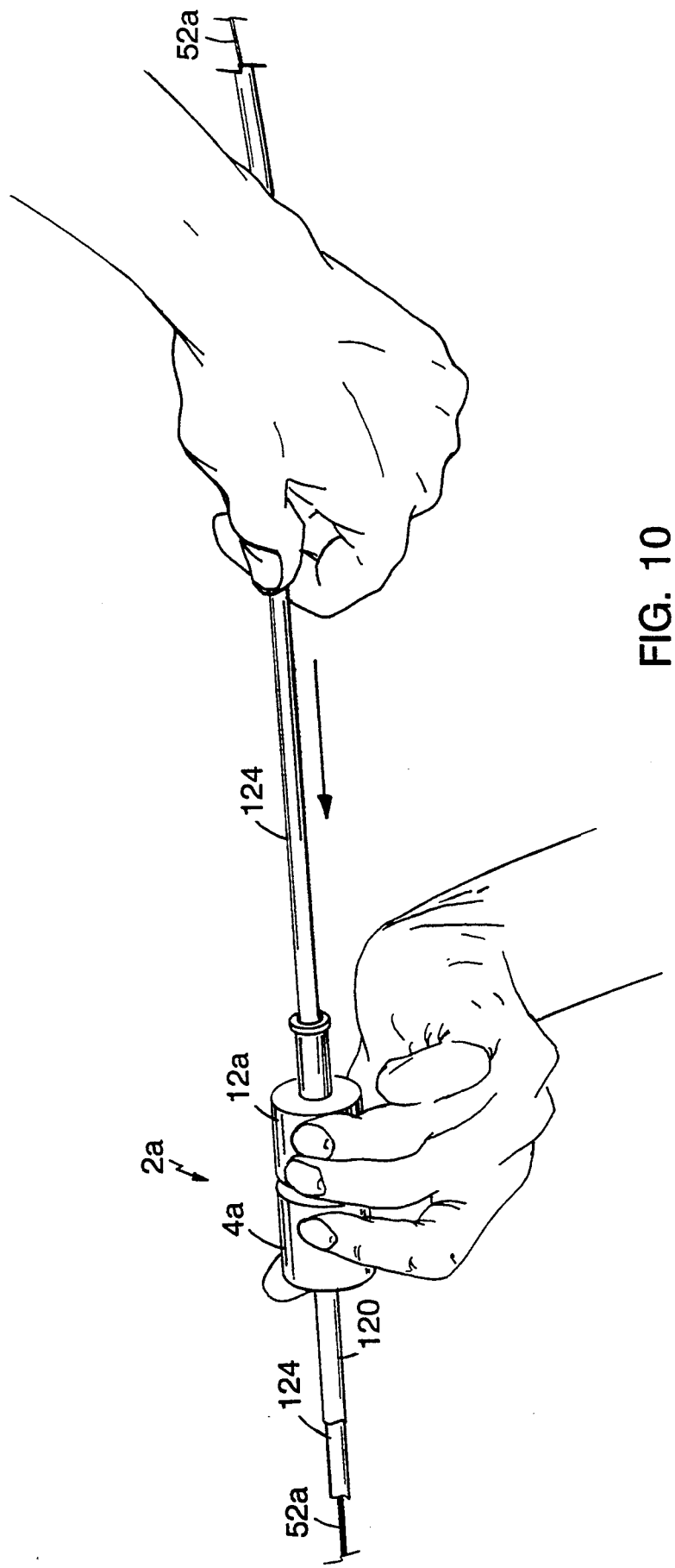

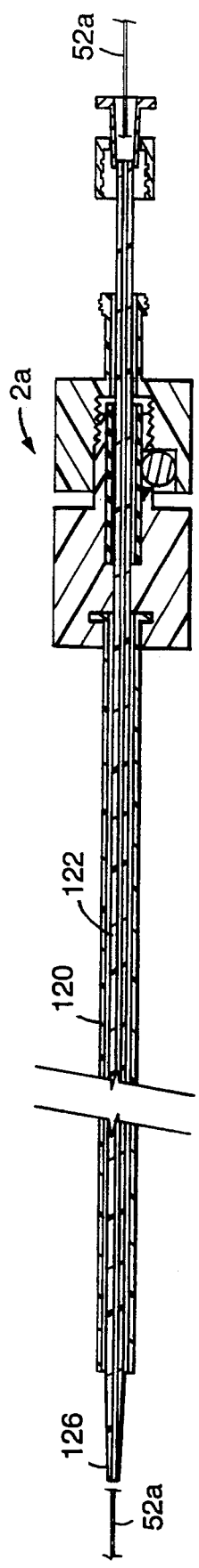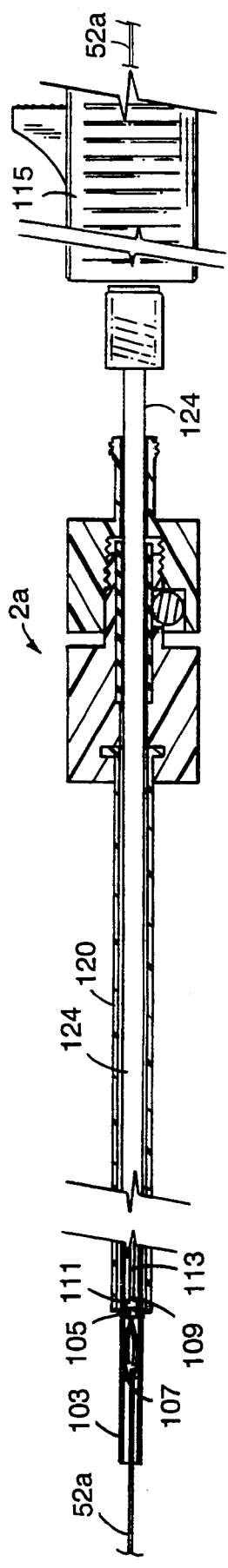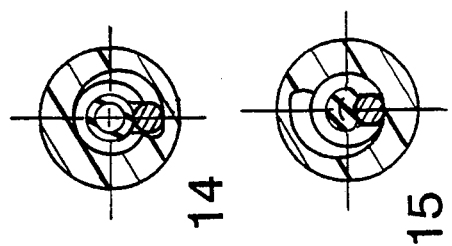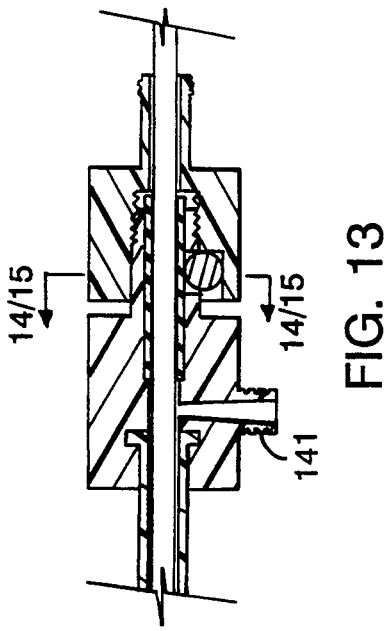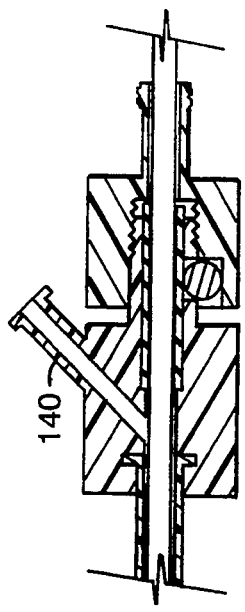

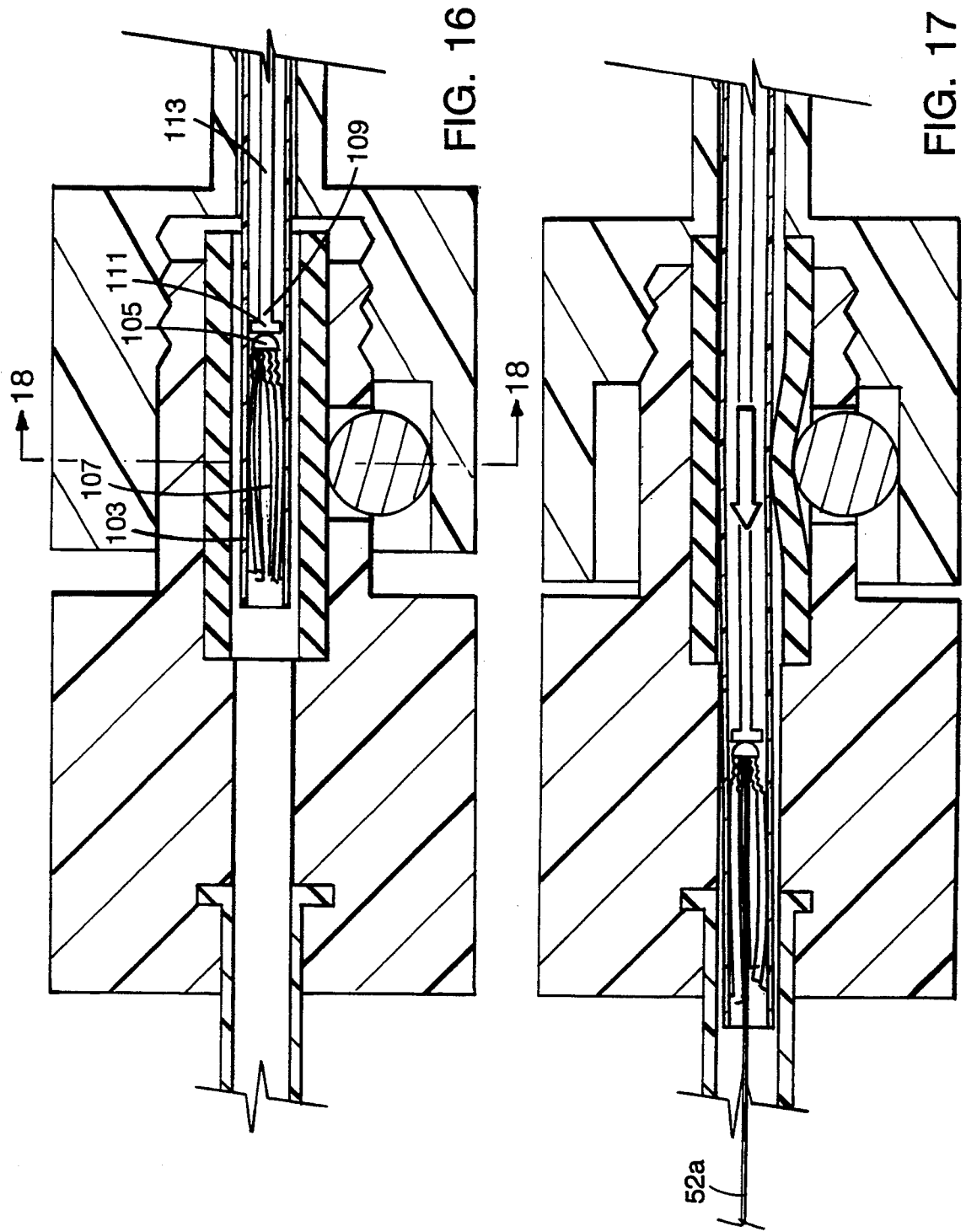

CATHETER INTRODUCER SHEATH ASSEMBLY

This is a continuation of application Ser. No. 07/775,046, filed Oct. 11, 1991, now abandoned.

FIELD OF THE INVENTION

This invention relates to through-channel valves and the like for medical applications, in particular, for the control of fluids and devices passing in or out of a patient's body. Operation of prior devices to some extent has been awkward and required more hand actions and the presence of more personnel than at times has been desirable.

BACKGROUND OF THE INVENTION

Catheters are placed inside blood vessels and body cavities, typically by being slid over guidewires. During placement, some way is needed to prevent backflow of blood or other fluid from the proximal end of the catheter. Many times it is also desirable, with minimum steps and effort, to attach a hand syringe to the proximal end of the catheter, open the catheter valve, inject fluids through the catheter and then remove the syringe and close the system. Many other applications require closure of a through-passage to, for example, control the flow of fluids as by a stopcoak or to grip a device, such as a guidewire, to provide a handle to enable working the wire to achieve its insertion and accurate placement in the body.

While it is well known to use luer fittings for attachment of medical instruments, e.g. a syringe to a catheter, valves controlling flow that use luer fittings generally do not have through-passages and also, for the most part, require separate activating motions.

The attachment of an external instrument such as a syringe to the passageway of a closure device in a manner that also opens the closure device is also known, but in a form that has had significant limitations. Such a device, for example, is described in U.S. Pat. No. 4,243,034. The described device relies on an axial sliding motion for making the attachment and opening a valve by releasing one or more balls from depression into the wall of a resilient tube. This device is neither as simple nor as effective as desired by those in the field, and also fails to meet all needs for single-handed operation in flow-control devices.

Other known closure or wire-gripping devices provide partial benefits but fail to combine all desirable features in one unit. For example, one type of device, known as a Tuohy-Borst closure, comprises a cap which, when screwed on, axially compresses a captured thick-walled tubular segment (a grommet) to seal a passage through the tubular segment. This device is disadvantageous in that it requires many turns to seal the passage.

SUMMARY OF THE INVENTION

An object of the invention is to provide an improved device for closure of a through-passage for use, for example, as a valve for a catheter or as a gripping member for a device such as a guidewire placed in the through-passage or channel. Another object is to provide a closure device of a simple, rugged, inexpensive and durable construction that will not inadvertently disassemble by the activating motions. It is a further object to improve on the operation and configuration of closure devices for attachment and detachment to medical components, such as the attachment of a syringe to a catheter.

These objects are realized according to one aspect of the invention by a closure device based upon rotation of a rotary cam to displace a compression member against the side of a resilient tube.

According to one aspect of the invention, a catheter introducer sheath assembly is provided comprising the combination of an elongated, flexible introducer sheath defining a passage and a closure device, the introducer sheath being joined to the distal end of said closure device, and the passage through the sheath and a through-passage through the closure device having diameters sufficient to pass a respective catheter therethrough.

The closure device comprises the combination of a resilient member at least partially defining the through-passage of the closure device, with the passage having an axis; and a body that includes first and second relatively rotatable body portions. The first body portion is stationary with respect to the resilient member, and the second body portion includes an internal cam having a cam surface oriented about, and spaced from, the axis of the passage. The cam has a first surface portion disposed relatively closer to the axis than a circumferentially spaced second surface portion. A compression member is positioned in a radially extending aperture in the first body portion and is biased radially outward by the resilient member to maintain contact with the cam surface. The members of this combination of the closure device are cooperatively related to enable adjustment of the radial compression of the resilient member for closing or opening the passage by relative rotation of the second body portion with respect to the first body portion to position, in dependent manner, the compression member radially closer to, or further from, the axis to close or open the passage or to engage, with desired tightness, a catheter or guidewire extending or sliding through the closure device and sheath.

Preferred embodiments of this aspect of the invention have one or more of the following features. The passages through the closure device and the attached sheath are sized to pass a catheter containing a vena cava filter and a stabilizer for placement of the filter. Preferably, the passages are of the order of ⅛ inch or greater in diameter. It is also preferred that the compression member be adjustable by manual manipulation of the proximal body to selected intermediate rotatable positions relative to the distal body portion to cause the tubing member to lightly engage the sides of a catheter, being inserted through the catheter introducer sheath assembly, to impede outward blood flow along the sides of the catheter while permitting its slidable insertion.

In a preferred embodiment, the device of the invention is combined with a removable elongated dilator disposed in the sheath and having a tapered distal portion extending distally beyond the sheath. The dilator has a small axial passage which enables the dilator, sheath and closure device to be slid over a pre-placed guidewire for guiding the sheath into a predetermined position.

In a second aspect of the invention, a catheter introducer kit is provided comprising in combination any one of the devices of the combination assembly given above, and further having one or more of the following features. The kit includes a catheter containing a vena-cava filter and a stabilizer for placement of the filter, with the passages through the sheath and the closure device having a diameter sufficient to pass the catheter therethrough. Preferably, the catheter introducer kit includes a dilator having a small axial passage enabling the dilator, sheath and closure device to be slid over a pre-placed guidewire for guiding the sheath into a pre-determined position.

Another preferred embodiment of both the first major aspect of the invention and of the first embodiment thereof as above described, has the following additional features. A stop surface is defined at the end of the second cam surface portion arranged to engage the compression member and stop relative motion apart of the body portions when the compression member reaches the passage-opening position. The first and second body members are further constructed to engage each other and stop threaded-together motion when the compression member reaches the passage-closing position. Preferably, the first surface portion of the cam positions the compression member radially to completely close in a fluid-tight manner the through-passage, and the second surface portion positions the compression member to fully open the through-passage for fluid flow. The cam defines a smooth spiral-form member. Also preferably, the rotatable body portion includes a first stop member which is engaged by the compression member and prevents disassembly by blocking further relative rotation of the body portions. Also, preferably a side channel is included distal of the axial position of the compression member and the rotatable body portion has an external surface exposed for engagement and rotatable operation by the hand of the user.

BRIEF DESCRIPTION OF DRAWINGS

FIG. 2 is a longitudinal cross-sectional view of the medical closure device of FIG. 1 in the open position, while

FIG. 2B is a longitudinal cross-sectional view of the closure device of FIG. 1 in the closed condition, while

FIG. 3 is an exploded view of the closure device of FIGS. 1 and 2;

FIGS. 4-4G illustrate steps in the assembly of the device, where FIGS. 4-4B are longitudinal cross-sectional views and FIGS. 4C-4G are a series of cross-sections, similar to FIG. 2A, taken through the center of the compression member at a sequence of rotary positions of the proximal body portion during assembly;

FIGS. 7A-7D illustrate an alternative embodiment of the device with an angled side arm for access to the through-passage distal of the point of closure (views 7A and 7C are transverse cross-sectional views; views 7B and 7D are longitudinal cross-sectional views);

FIGS. 8A and 8D illustrate an alternative embodiment of the device with a 90 degree side arm entry for access to the through-passage (views 8A and 8C are transverse cross-sectional views; views 8B and 8D are longitudinal cross-sectional views);

FIGS. 9 and 9A illustrate use of the device as a gripping member with its attachment to a guidewire;

FIG. 10 is a perspective illustration showing combination of a larger closure device according to the invention with an introducer sheath and use of the device as a gripping and closure control device in introducing a catheter, (containing a vena cava filter) through the device and sheath, into the vena cava of a patient;

FIG. 11 is a view in longitudinal cross-section of a catheter introducer assembly comprising a closure device, attached introducer sheath and dilator within the sheath;

FIG. 11A is a view similar to FIG. 10 of the introducer sheath of FIG. 11 through which a placement catheter containing a vena cava filter and stabilizer assembly extends;

FIG. 12 illustrates in longitudinal cross-section the device of FIG. 11 modified to have an angled side arm access port connected to the through-channel distal of the point of closure;

FIG. 13 illustrates in longitudinal cross-section the device of FIG. 11 modified to have a 90 degree side arm access port connected to the through-channel distal of the point of closure;

FIGS. 14 and 15 show in cross-section along line 14/15-14/15 of FIG. 13 relative positions of the compression member and the resilient tubing in open and closed positions, respectively;

FIGS. 16-17 show in cross-section the device of FIG. 11 with details of the vena cava filter and stabilizer within the placement catheter as they are inserted through the closure device and introducer sheath;

FIG. 18 shows in cross-section along line A—A of FIG. 16 the positions of the cam and other components in clamping and sealing relationship upon a guide wire while

DETAILED DESCRIPTION OF THE PREFERRED EMBODIMENTS

Structure

Figure 1:
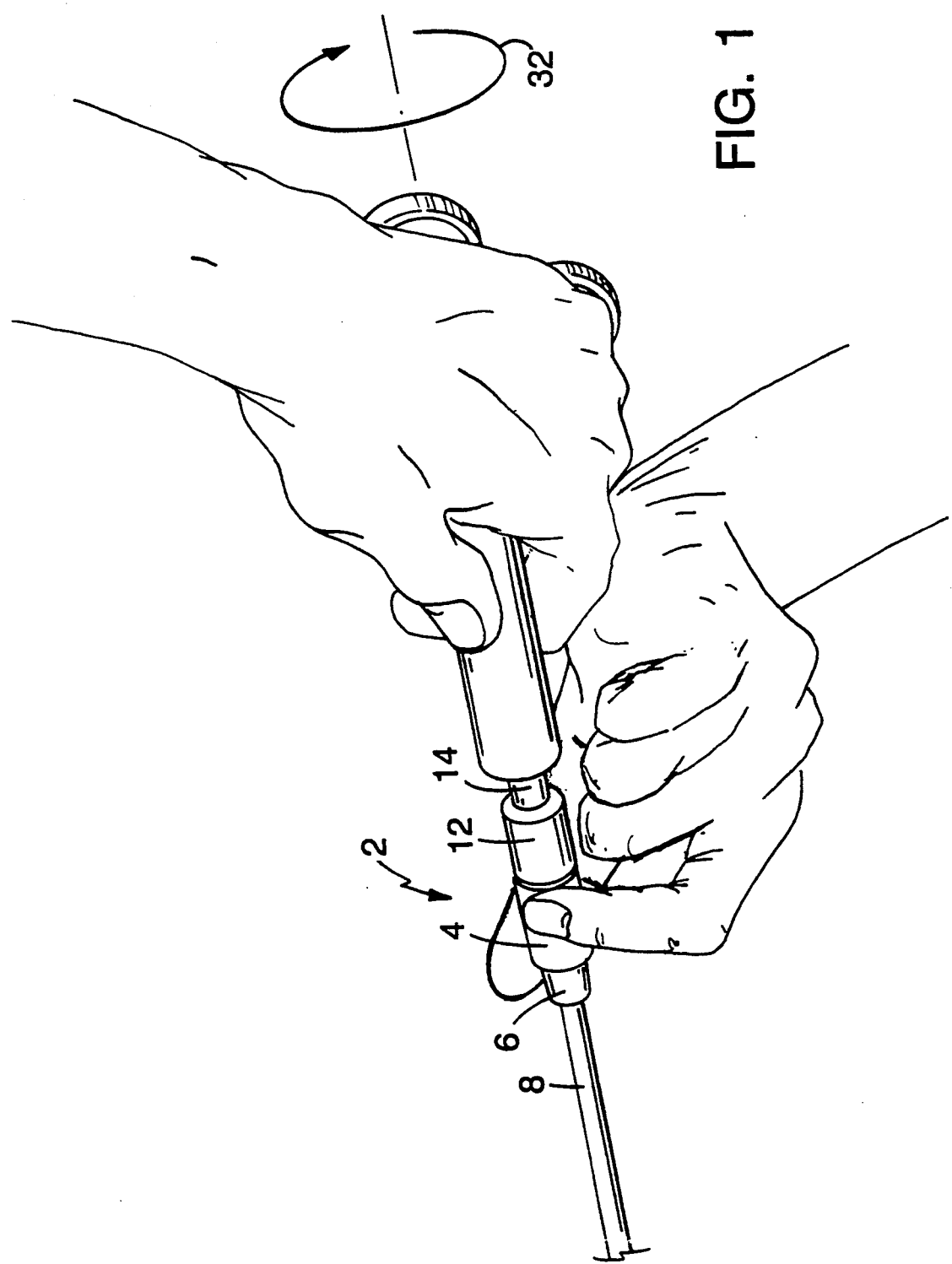
FIG. 1 is a perspective illustration of a user holding the distal part of the closure device while connecting a syringe to the proximal part of the closure by turning.
Figure 2A:
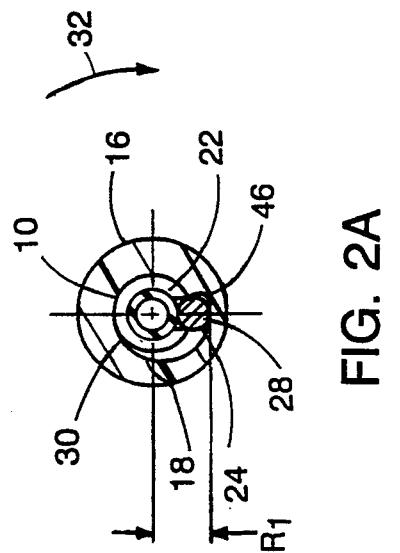
FIG. 2A is a transverse cross-section of FIG. 2 along line 2A—2A.
Figure 2C:
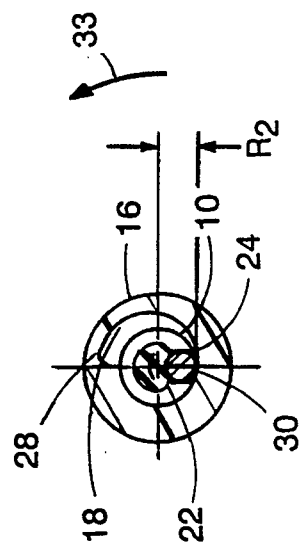
FIG. 2C is a transverse cross-section of FIG. 2B along line 2C—2C.
Figure 2:
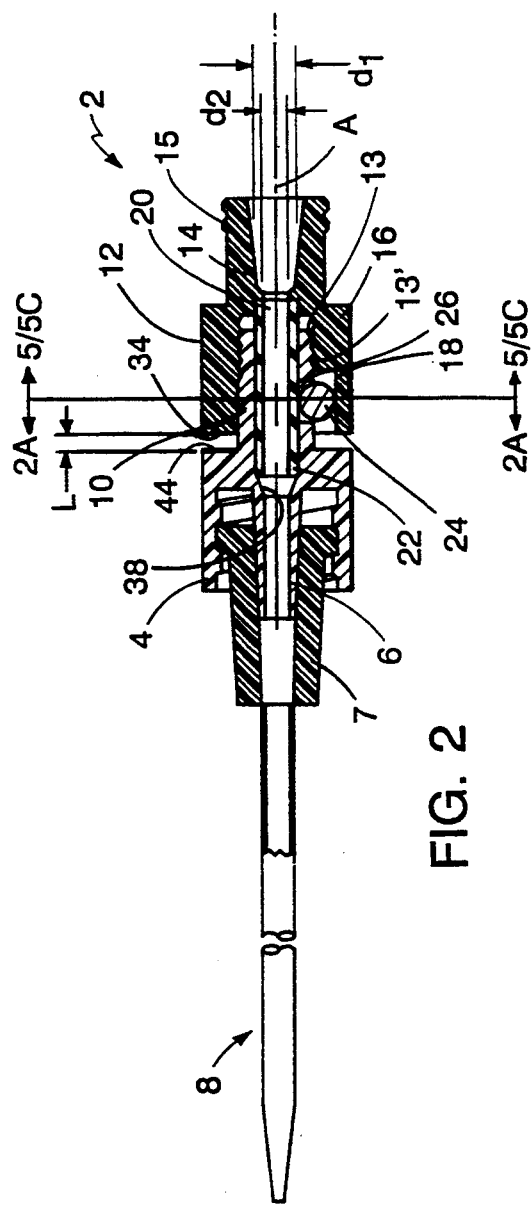

Referring to FIGS. 1 to 3, medical closure device 2 includes a distal body member 4 having a distal end 6 configured as a male luer locking member for attachment, for example, to the hub 7 of an angiographic catheter 8 (5 French), and a proximal end 10 which is threadably (threads 13) attached to a proximal body member 12. The proximal body member includes a proximal end 14 which is adapted as a threaded (threads 15) female locking luer attachment and a distal end 16 that includes threads 13'. Overall length of this embodiment is about 3 cm and diameter about ½inch as described below.

The external cylindrical surface of the body member provides a convenient gripping surface for hand operation of the closure device.

The distal end of the proximal body includes in its interior an inner cam 18 having a cam surface that is circumferentially arranged about axis A of the device. Channel 20, having an axis A, extends through the device (FIG. 2). A tubing member 22, preferably silicone tubing, is positioned in the channel. In this preferred embodiment, the silicone tubing has, in unstressed condition, an outside diameter $d_1$ of approximately 0.150 inch, an inside diameter $d_2$ of 0.060 inch, and a wall thickness of about 0.045 inch. When installed in the body member 38A and taper 42A, the tubing is compressed and supported by the walls of the body so that it, in open condition, has an outside diameter of 0.141 inch and an internal diameter of 0.055 inch.

A valve is formed by a spherical compression member 24, preferably a stainless steel ball with a diameter of about 0.125 inch, which is biased radially outward by tubing member 22 such that the compression member maintains contact with cam 18. As illustrated particularly in FIG. 3, compression member 24 is positioned in an aperture 26 in the proximal portion 10 of distal body 4 to prevent axial motion of the compression member, but permit and guide its radial movement. Preferably, the aperture has a diameter $d_3$ of 128 inch, and a depth $d_4$ of 0.056 inch.

To effect opening of the through-passage, the relative rotation of distal body 4 and proximal body 12 in direction 32 is adjusted such that the compression member is positioned along portion 28 of cam surface 18, furthest in radial position, distance $R_1$, from axis A, as illustrated in FIGS. 2 and 2A. The cross-sectional views of FIGS. 2A and 2C illustrate that when rotated clockwise from the closed position (FIG. 2C), the movement of the proximal body member causes the compression member to disengage its compression of the tubing in a linear fashion by action of the cam surface, until a point is reached when the compression member no longer compresses the tubing and is positioned on cam surface portion 28. The compression member then comes into abutment with butt stop 46 (FIG. 2A) formed by the proximal body, preventing further rotation.

Figure 2B:
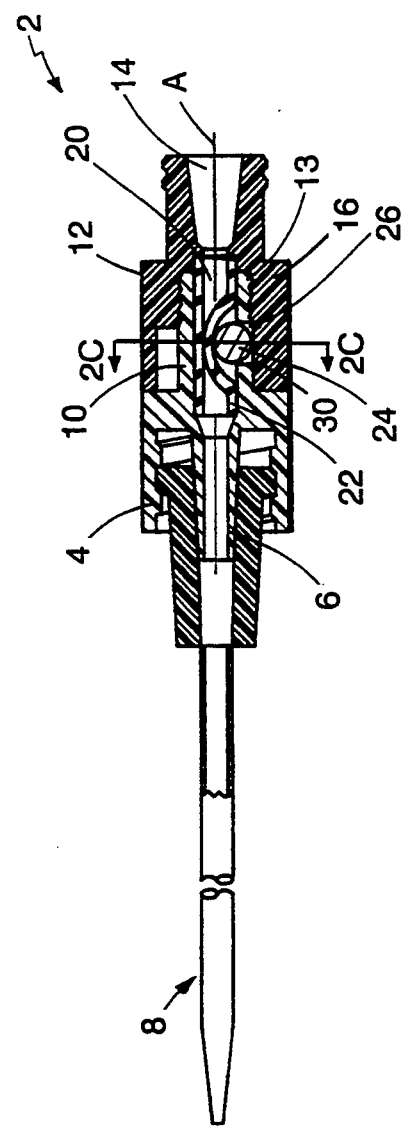

Similarly, to effect closure of the through-passage, proximal body member 12 is rotated counter-clockwise relative to distal body member 4 (arrow 33 on FIG. 2C) causing compression member 24 to be positioned on portion 30 of the cam which is closest, dimension $R_2$, to axis A of the through-passage. This moves the compression member radially inward to compress the tubing member 22 and reduce and close the opening of the through-passage, as illustrated in Figs. 2B and 2C.

Left-handed threading 13 and 13' is used in joining the distal and proximal body portions. Therefore, as proximal body member 12 is rotated in a counterclockwise direction, as viewed from the proximal end of the closure device (in the "screw-on" direction, indicated by arrow 33), the proximal body member moves axially distally, i.e., closer to distal body member 4. The cam is oriented such that full closure of the free passage is reached at a point of the counter-clockwise rotation when surfaces 34 and 44 of the proximal and distal body-members, respectively, butt with one another, giving the feel also of a definite stop point for the fully closed position.

Thus, in this embodiment, in which the closure device is used as a stop cock with a syringe attachment, the cam is oriented such that opening of the through-passage is effected by clockwise rotation and closure of the through-passage is effected by counter-clockwise rotation of the proximal body member, as viewed from the proximal end of the device. This arrangement advantageously allows the user to attach the syringe and open the passage, or close the passage and remove the syringe, with a single motion.

The axial travel of the proximal body member between the fully open and fully closed positions (FIGS. 2A and 2C) is indicated by gap "L" (FIG. 2). In the preferred embodiment, this distance is about 0.030 inch and is covered by an approximate 180° rotation of the proximal body member. During rotation, the portion of the cam surface contacting the ball-form compression member lies at a radial distance from the axis A that changes by a similar dimension,0.030 inch between open and closed positions.

Luer connector 14 (with Luer taper from dimension $d_1$ to $d_2$ and external Luer threads) is configured in the common manner, to require a clockwise rotation of an external component, such as a syringe, for attachment to the closure device 2. With this rotation arrangement and the closure device in the closed condition initially, the proximal body member resists relative rotation when the syringe is being attached because the tubing member under compression by the compression member produces frictional drag. The syringe thereby can be initially lead on to the luer thread. The resistance of the cam arrangement is overcome when the component becomes partially engaged on luer connector 14 by the clockwise rotation and resistance of the luer connection increases as normally occurs. At that point, further clockwise rotation of the syringe causes simultaneous clockwise rotation of the proximal body portion, and channel 20 is opened as the compression member moves along cam surface to cam portion 28. When the compression member reaches the butt stop 46, the proximal body portion is stopped from rotation, and further clockwise rotation of the syringe enables the luer connection to reach its final locked position.

When, after use, the syringe is to be removed, the syringe is subsequently rotated in the counter-clockwise direction. The proximal body portion 12 rotates simultaneously with the syringe, because of the locking friction of the luer in its locked position, (there is also less resistance exerted on cam surface 18 by compression member 24 when the tubing, in open position, is not significantly compressed). After the proximal body portion has been rotated such that compression member 24 is moved into contact with cam portion 30 and the through-passage is closed, surfaces 44 and 34 of the two body members move into abutment by the left-handed mounting threads, establishing a definite stop point indicative of the closed condition of the through-passage. The syringe is then disconnected by its further rotation in the same direction to overcome the resistance of the luer lock.

In an embodiment where the closure device is used with a syringe as a connected component, the device preferably has an outside diameter of about 0.445 inch and is approximately 3 cm. in length. A typical syringe may have an outside diameter of 0.75 inch and length of 10 cm. A particular advantage of the preferred embodiment incorporating the described rotary cam/ball valving arrangement described is its dual operability, i.e., its ability to be opened or closed either by hand or by attachment of an external component such as a syringe.

Another particular advantage is that, once assembled, the simple construction of the device prevents its disassembly. Clockwise rotation of the proximal body member 12 causes the cam surface to ride along the compression member to effect opening of the through-passage. When the relative rotation of the distal and proximal body members places portion 28 of the cam surface in contact with compression member 24, further rotation is prevented by butt surface 46 which engages the axially-stationary compression member. This prevents further clockwise rotation and any disassembly of the device in this direction.

Similarly and conversely, when the relative rotation is such that the compression member 24 or ball is adjacent to cam surface portion 30 closest to axis A, end 34 of the proximal body member engages surface 44 of the distal body member, thereby preventing any further rotation and possible damage to the compression member or body members.

With rotation being thus limited in either direction, disassembly of the device by rotation of threads 13 and 13' is entirely prevented.

This feature of having a device of few and rugged parts that is incapable of being disassembled is of particular importance since it makes the device virtually fail-safe because it can neither be overtightened nor disassembled which could lead to loss of parts, introduction of dust, blood, etc.

Preferably, markings are on the body of the closure device so that the operator can tell whether the device is in the ON or OFF position and know the direction for rotation to the other setting.

Referring to FIG. 3 as well as FIGS. 4 to 4G, assembly of an embodiment of the device is illustrated.

Assembly of the distal body member with the proximal body member involves an interference fit of the elastomeric tube with the two slightly tapered female connections, one on the proximal end of the distal body member 38A and one on the distal end of the proximal body member 42A. The significant taper 38 of channel 20 serves to accommodate the thickness of the tube, to prevent tube movement while allowing for variation in the length of the tube, and to facilitate insertion of a guidewire or catheter through the channel. The taper of the ends of the channel in each body portion which the tube ends enter for their interference fit are tapered only slightly for achieving the desired interference. The tubing is first inserted into the channel of one member using a drop of silicone oil on the tube during assembly. This facilitates the joinder while also assisting in the combined radial and axial compression sealing of the tubing within the channel. Although oil is not needed on the compression member and in the recess within which it operates, some of the oil from the tubing may come into contact with the compression member which presents no problem and can benefit smooth operation of the closure device.

The tubing, due to the surrounding support provided by the housing walls that define channel 20, is capable of withstanding fluid pressures of greater than 1000 psi. Thus the device may be used for example, to handle pressures of 300-400 psi where a contrast media is to be injected rapidly from a syringe, and pressures up to 1,050 psi when used with a contrast media injector. High injection pressure is required in such an application so that the contrast media is rapidly totally injected and thus it is not dispersed. The pressure is needed to overcome the flow resistance of the relatively long path it must travel to reach the point in the body for the intended fluoroscopic medical observation.

In assembly, proximal body 12 is aligned with, and partially threaded onto, the proximal portion 10 of distal body 4 such that end 34 is roughly in alignment with the edge of aperture 26 in which the compression member is placed (FIG. 4). Tubing member 22 has at this point already been positioned in the distal body member 4. The length of tubing member 22 (overall length about 0.480 inch) extends from a taper 38 in distal body 4 to beyond (about 3.0 mm) the most proximal end 40 of the distal body member 4, so that when assembly is complete, the proximal end of tube 48 reaches surface 42 to position the tube, though the main sealing effect is achieved by interference with the taper of the associated body portion into which the proximal end of the tube fits. Use of the resilient tubing in this manner produces both a fluid-tight and an air-tight seal, and allows operation with the high fluid pressures mentioned.

In the next step of assembly, compression member 24, here in the form of a ball, is positioned in aperture 26 (FIG. 4). The compression member's diameter is larger than depth $d_4$ of the aperture on the proximal portion of the distal body member, so the compression member will naturally extend beyond the outer edge 43 of proximal body portion 10 of distal body 4, being biased outwardly by the resilient tubing member 22 (FIG. 4). The compression member also extends beyond cam surface 18, even with the cam surface rotated to a position radially furthest from axis A, i.e. in open position.

To proceed with assembly, the compression member is then depressed radially, for example with the finger, so that it does not extend beyond surface 18 and, simultaneously, proximal body portion 12 is rotated in the "screw-on" direction counter-clockwise a number of turns such that its distal end overlaps the compression member (FIG. 4A). Whereas the rotatable body portion defines a spiral-form cam surface with an abrupt transition from the end of the cam surface portion 28, furthest from the axis, to a portion of the body member closest to the axis, continual rotation during assembly of the body portion in screw-on direction is permitted by the parts. The compression member is gradually progressively compressed against the resilient member until the maximum is reached at which state it remains until sufficient further rotation causes the abrupt transition and surface portion 28 of the cam surface to register with the compression member, (FIG. 4B) and permit spring outwardly of the compression member to permit repetition of the rotational motion, (whereas opposite rotation of the rotatable body portion along the threads is limited by stopping of the compression member against the abrupt formation, butt surface 46, of the rotatable body portion). FIGS. 4C through 4G show various positions of the cam surface relative to the compression member during the assembly stages. As discussed, because of stop surfaces 34, 44, 46 (FIGS. 2 and 2A), the device, once assembled, cannot be disassembled by rotation in either direction.

Figure 5:
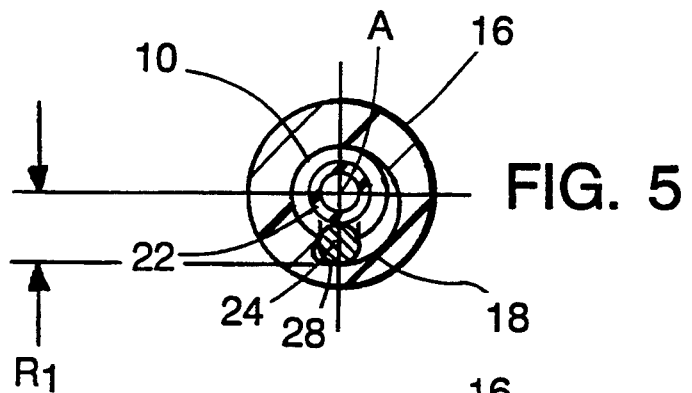
FIGS. 5-5C taken in the direction of Line C—C in FIG. 2 illustrate gradual closure of the through-passage during operation showing positions of the cam surface and the radially moveable compression member.
Figure 5A:
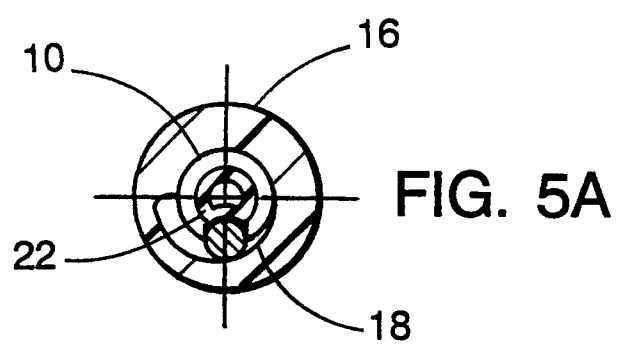
Figure 5B:
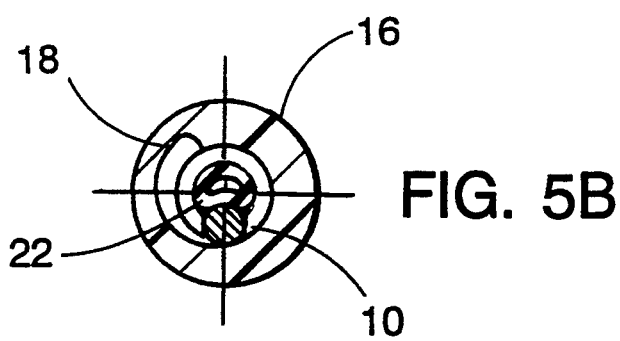
Figure 5C:
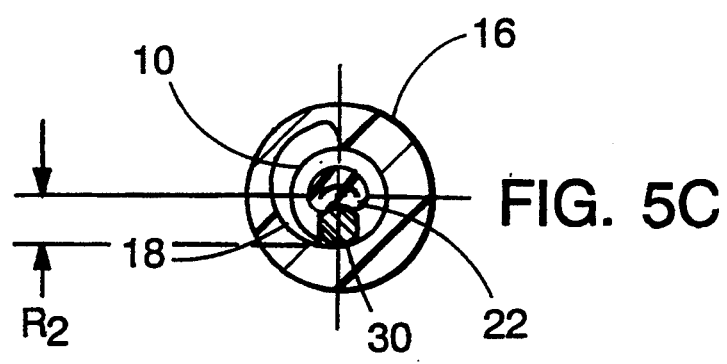

Continuous gradual control of the size of the through-passage is illustrated in the series of FIGS. 5 to 5C, which show, in cross-section taken along line C-C of FIG. 2, cam surface 18, compression member 24, conformable tubing member 22 and axis A. As illustrated, the distance from cam surface 18 to axis A varies continuously along a spiral path of the cam from a maximum distance $R_1$ (about 0.177 inch) near end 28 (FIG. 5) to a minimum distance $R_2$ (about 0.107 inch) at end 30 (FIG. 5C).

The conformable interior of the resilient tubing provides a seal about an object, such as a guidewire, if present in the through-passage when the device is in the closed position.

Further, in the embodiment described in the figures above, the use of a freely rotating spherical compression member or ball allows for through-passage opening adjustments by slight rotation in either direction.

Figure 6:
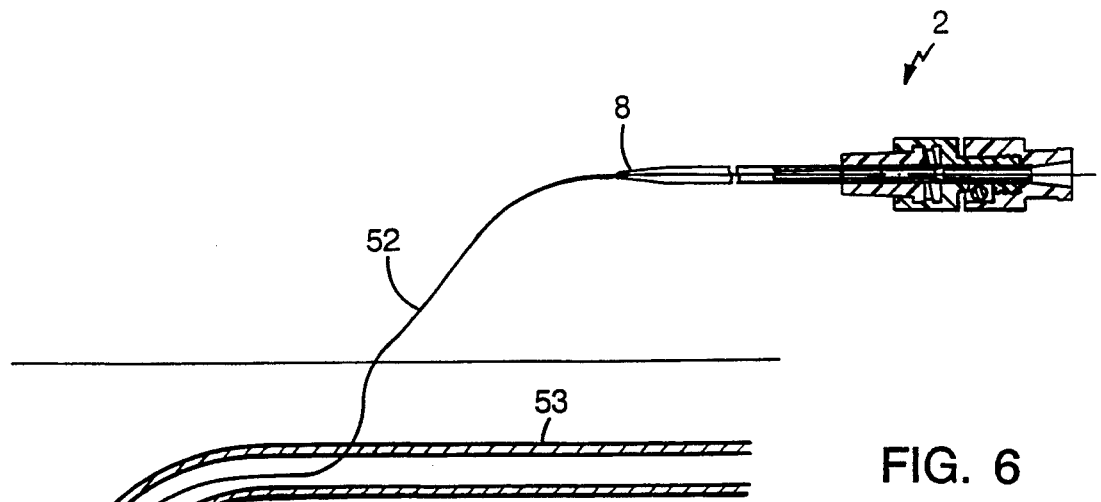
FIGS. 6 to 6E illustrate use of the device in a catheterization operation.
Figure 6A:
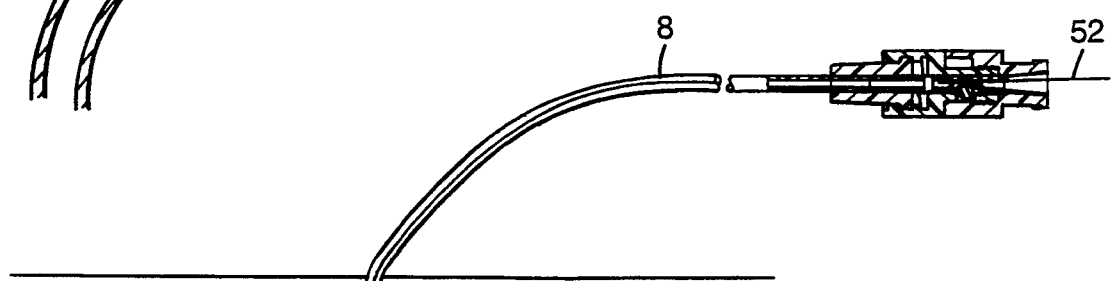
Figure 6B:
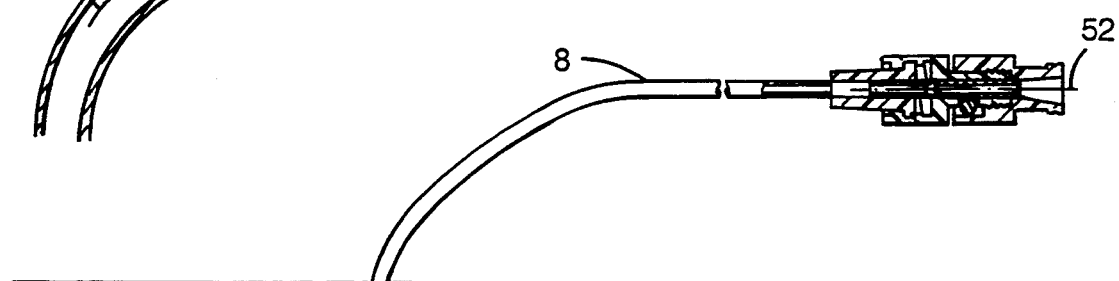
Figure 6C:
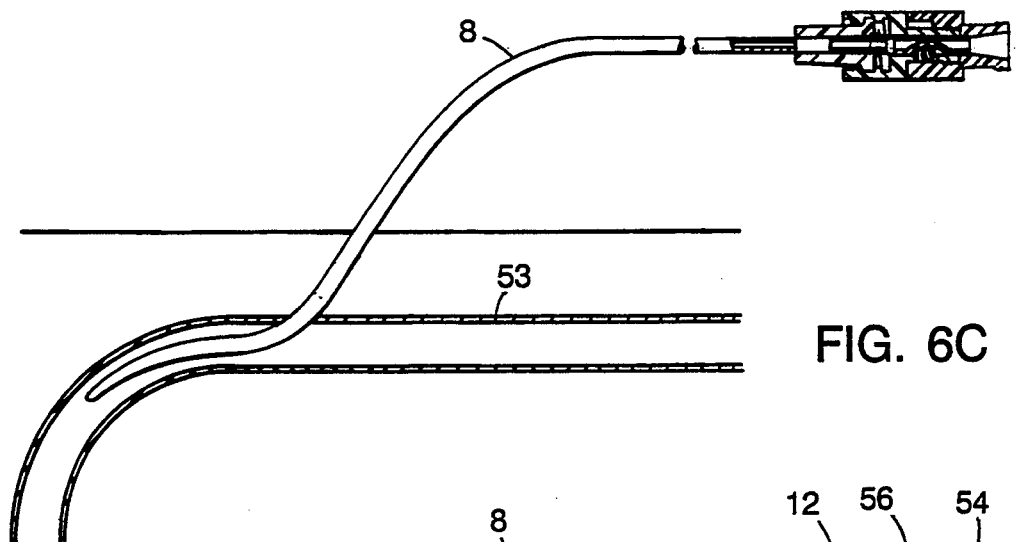

One particular use of the closure device is in the medical field for providing through-channel access to a catheter, such as an angiographic catheter. Referring to FIG. 6, in a typical catheterization operation such as an angiographic procedure, a guidewire 52 is positioned at the location of a desired arterial passageway (FIG. 6), such as the femoral artery for example, using an introducer needle (not shown) applying the Seldinger technique. An angiographic catheter 8 having attached thereto the closure device 2, is threaded over the guidewire 52 such that the catheter is positioned in the artery 53 (FIG. 6A). For this operation the closure device is in the open position, or alternatively, in a partially opened position to minimize backflow of blood alongside of the exterior of the catheter from the artery. The guidewire and catheter may be further positioned within the artery by manually rotating the proximal body member to the closed position, while gripping the guidewire 52 (FIG. 6A). The guidewire, catheter and device can thus be moved and torqued as a single unit to aid positioning as well as avoid punctures and other disturbances of the vessel (arterial passageway). With the catheter properly positioned, the device may be placed in the open position, again by manual rotation, to open the through-passage and allow removal of the guidewire (FIG. 6B). After removal of the guidewire, the valve is manually closed (FIG. 6C).

Figure 6D:
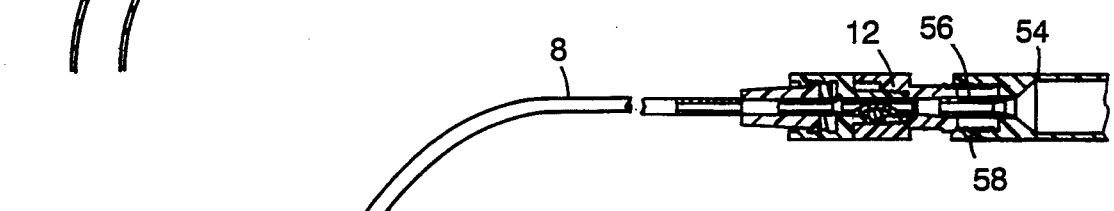
Figure 6E:
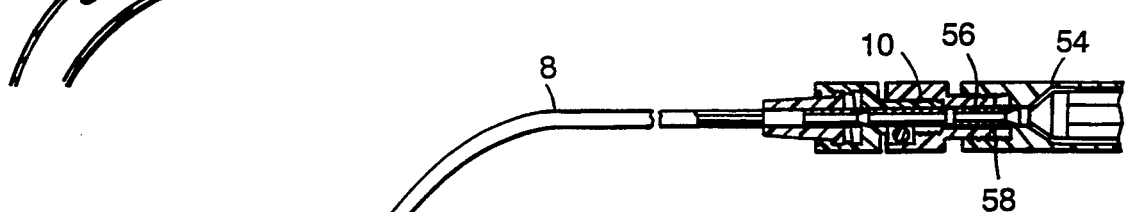
Figure 18:
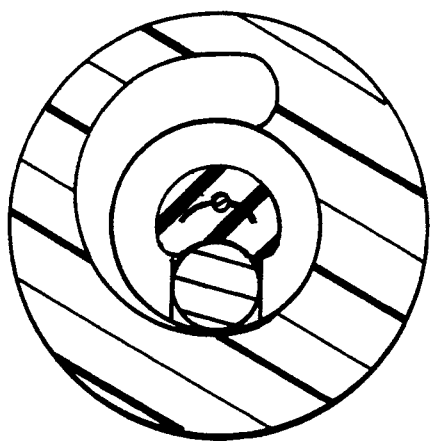
Figure 19:
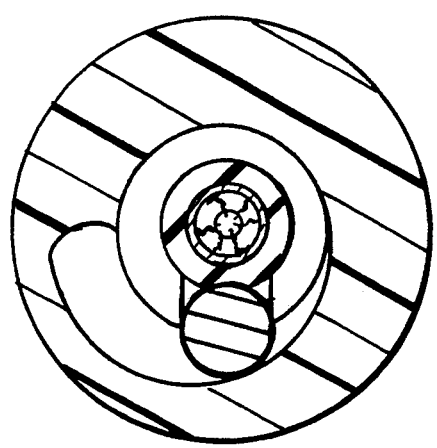
FIG. 19 is a similar view showing the cam in partially closed position in sliding/sealing relation to the filter introducer catheter during insertion of the introducer catheter into the body.
Figure 20:
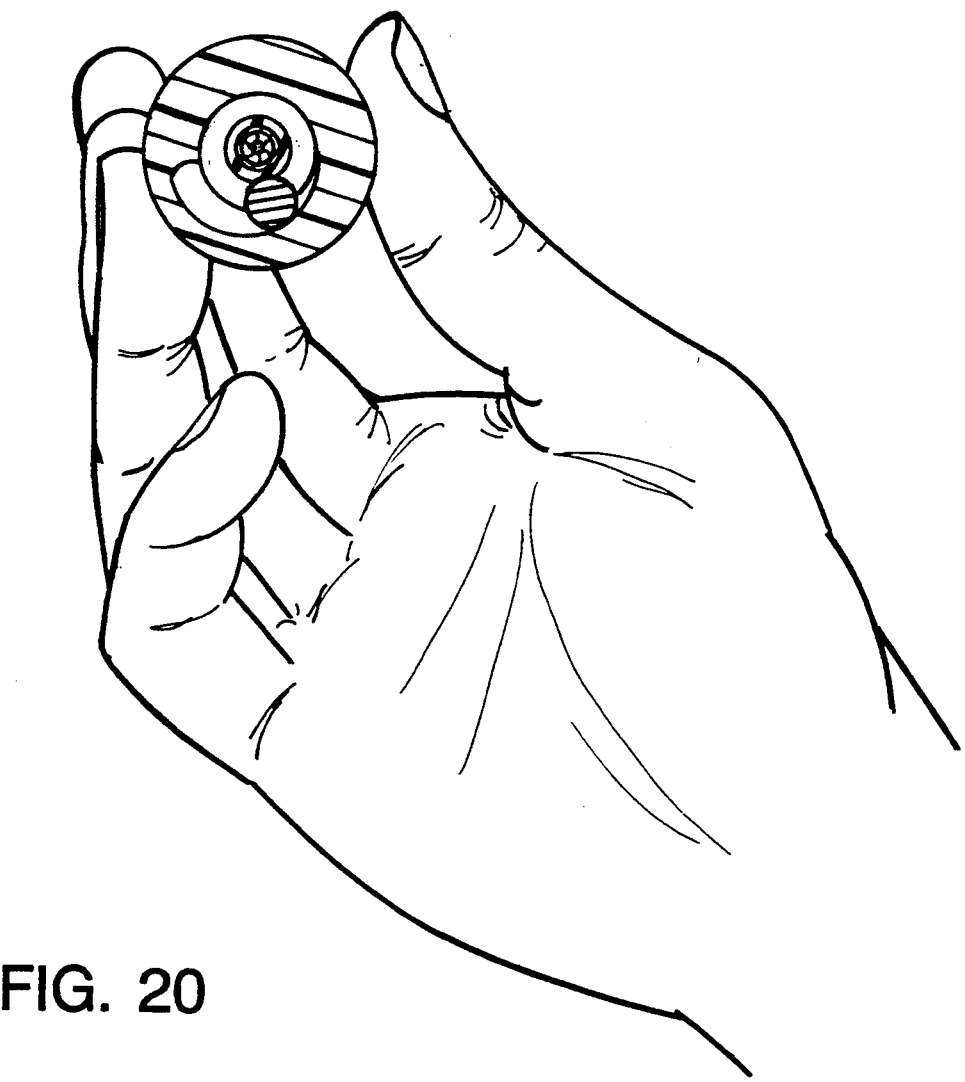
FIG. 20 illustrates relative size of the device in cross-section by depicting it being held by a user who is adjusting the closure by one hand.

In the embodiment of FIGS. 6 through 6E, the closure device can have the catheter permanently attached, as by insert molding, or removably attached as by matching luer connectors, to the distal end of the distal body member.

During the catheterization procedure, it is often desirable to inject fluids, such as contrast fluids for radiographic imaging, through the catheter. To effect injection, a syringe 54 with a distal end 56 adapted as a male luer lock fitting having locking thread 58 (end thread) is connected to the female luer adaptor 14 defined at the proximal end of the proximal body portion 12 by clockwise, "screw-on" rotation of syringe 54. The syringe rotates relative to the proximal end 12 before reaching a pre-engagement position (FIG. 6D). After reaching this position, at which point locking thread 58 is initially engaged, further rotation of the syringe causes simultaneous rotation of proximal body member 12 thereby automatically effecting opening of the through-passage (FIG. 6E). When the compression ball reaches the end of the cam surface and engages butt surface 46, rotation of the distal body portion is stopped and further rotation of the syringe seats the luer lock. Injection of fluid can then be commenced. After injection, rotation of the syringe in the opposite, counter-clockwise direction causes simultaneous rotation of proximal body member 12 of the device, thereby automatically closing the through-passage. After the through-passage is completely closed, further rotation of the proximal portion is prevented by butting of the body portions together, as discussed above, and the syringe may then overcome the resistance of the luer lock and rotate relative to the proximal portion and be unlocked and removed.

Referring to FIGS. 7A through 7D, another embodiment of the device is shown to include a side arm 70 through which fluids may be injected, even after closure of the through-passage (FIG. 7C/7D). Such a side arm may be provided on the distal portion of the device and include luer threads for connection to a catheter. This embodiment would be particularly useful in contrast injection after a guidewire passing through the closure device is locked into place.

Referring to FIGS. 8A through 8D, another embodiment employing a side arm 80 at a right angle to the through-passage is illustrated, in which a male locking luer 82 is constructed integrally therewith.

Referring to FIGS. 9 and 9a, the closure device 2 is shown for use as a quick hub attachment, by closing the channel 20 upon, for example, an elongated member. The elongated member 90 may be, for example, a small diameter guidewire, as shown, or a tube, and closure device 2 provides a convenient handle for the member as it is torqued during positioning in the body.

With the syringe or any other attachment to the proximal body member of the closure device removed, the device functions as a stop cock (though requiring counter clockwise rotation to close) for controlling flow through a tubing or other such elongated member 90, as shown in FIGS. 9 and 9A, thereby replacing conventional stop cocks and for which no additional drawing is necessary.

Where the automatic opening feature upon connection of a device is not to be employed, threads 13 and 13' may be changed to right hand threads to enable this through-passage stop cock and gripper to close with conventional right hand rotation.

In a very important further embodiment, referring to FIG. 11, a closure device 2a is provided of much larger dimension, (device 2a preferably having an outer diameter of about 1 inch, the tubing having an outer diameter of about 0.316 inch, and the through-passage having an inner diameter of about 0.170 inch) and having the direction of its spiral cam surface and the direction of the threads between the parts of the housing extending in the opposite direction (right handed). This device is connected, e.g. by insert molding, to a thin-walled sheath 120 of between 50 and 150 cm length to provide a catheter introducer sheath assembly, constructed to enable introduction of a placement catheter 124 for the placement of an element, such as a vena cava filter (one type of which is known as a Greenfield filter) into the body. (The closure device and sheath could be joined instead by any other means, e.g. matching luer connectors between the closure device and the sheath). The use of a vena cava filter for filtering out blood clots by its placement in the inferior vena cava is well-known in the medical field. See, e.g. U.S. Pat. No. 3,952,747 to Kimmell, and U.S. Pat. No. 4,817,600 to Herms et al. the texts of which are incorporated herein by reference. The general procedure followed in the embodiment to be illustrated is to use a guidewire (the guidewire may be routed into the desired position using the closure device of FIG. 2 as a gripping means).

Where a guidewire is used, the guidewire is routed through the vasculature in a manner where it can be watched fluoroscopically and manipulated accordingly. Thereafter the thin-walled sheath 120 with attached closure device 2a and containing an elongated flexible dilator 122, with exposed tip 126 (see FIG. 11) is introduced over the guidewire, and once placed, the dilator is withdrawn. Closing the valve of the closure device 2 forms an air-tight and fluid-tight seal around the guidewire, thereby preventing, for example, blood from flowing backwards through the sheath 122. Thus, the guidewire can be temporarily left in place inside the long flexible sheath when used with the closure device of the invention; reliable closure is established around the guidewire by an approximate one-half turn of the proximal body member relative to the distal body member by simple manual rotation of the proximal body portion by grip of the outer cylindrical surface.

The placement catheter 124 containing the vena cava filter 105 is then introduced via the through-passage of the closure device 2a as shown in FIGS. 10 and 16. For this purpose the proximal portion 12 of the closure device 2a is rotated to open position (in this case, using right hand threads, opening direction is counter clockwise.) After threading of the catheter 122 through the closure device 2a and sheath 120 has begun, as depicted in FIG. 10, the user manipulates the proximal body portion to slightly snug the elastomeric tube against the exterior of the catheter, sufficiently to reduce blood loss along the catheter but insufficient to impede desired sliding of the blood-lubricated catheter into the sheath, see FIG. 17.

The end portion of this catheter which first passes through the closure device is a metal sleeve 103 (FIG. 11a), within which is positioned the vena cava filter 105, characterized in part by its springy legs 107. This is delivered to the vena cava of the patient first by sliding the catheter through the closure device and the sheath and then drawing the sleeve proximally, releasing the filter from the end of the catheter. The use of a metal sleeve as the distal end portion of the catheter enclosing the filter facilitates release of the filter, which has outwardly springable legs, as shown from inside the catheter when the catheter is in position for final placement of the filter in the inferior vena cava.

The filter freely rests in the described metal sleeve of the catheter with a stabilizer 109 within the catheter 122 having a flat surface 111 immediately behind the filter. The stabilizer is connected to a tube 113, a sufficiently axially stiff structure to accomplish the stabilizing effect on the filter. When the catheter is positioned at the desired point in the vessel, the catheter 124 and its distal metal sleeve 103 is pulled proximally, while the stabilizer 109 remains stationary, by means of a reverse action trigger 115 attached to the proximal end of the proximal body member of the closure device. This reverse action operates so that pull-back on the trigger by the operator causes release of the filter from the catheter.

In the catheter placement embodiment of the invention, as mentioned above, the threads by which the proximal portion of the distal body member is connected to the distal portion of the proximal body member are right handed (reversed from the left-handed threading used in the syringe attachment embodiment of the invention). Thus in the catheter placement embodiment, the proximal body member is turned to the left (counter clockwise) relative to the distal body member to open the resilient silicone tubing. This open position is used for introducing the sheath, dilator and closure device over the guidewire which passes through the closure device and for introducing the catheter and contained vena cava filter into the sheath. The open (or partially open) position is also maintained during activation of a reverse action trigger at the proximal end of the catheter for deployment of the vena cava filter from the metal sleeve end of the catheter.

As shown in FIG. 12, this embodiment includes angled side arm 140 through which fluids may be injected after closure of the through-passage by the ball member. This side arm is located on the distal side of the device and includes luer threads for connection to a supply tube that communicates with an elevated source or a to a syringe. This embodiment is useful for flushing the space within the catheter introducer sheath with saline solution containing heparin, to prevent blood clotting which could block the through-passage and obstruct later insertion of the catheter containing the vena cava filter. Flushing may take place before, during or after deployment of the filter, as long as the through-passage is closed. The side arm may instead be disposed at a 90 degree angle to axis A of the device, as shown in FIG. 13 by side arm 141.

Alternative Embodiments

In conclusion, in its more general aspects the invention can be embodied in many forms too numerous to attempt to mention, as will be understood by the person skilled in the art. As examples only, the distal body member of the closure device could carry an integral, deflectable hinged member in place of the separate spherical compression element as described, as a valve component to be disposed between the cam surface of the proximal body member and the resilient tube to effectuate opening and closing of the tube. Also, although only one cam and associated compression member has been described, in its broader aspect the closure device of the invention is not so limited. For example, two cams could be used with two compression balls, hinged legs, cantilevered elements, or the like on opposing sides, to carry out the tube-opening and closing by means of displacement of the elements in the closure device of the invention by co-rotation of respective cam surfaces. Thus, although a ball-form or sphere has been described as the compression member in the device, the member does not necessarily have to be of that form, nor does it necessarily need to be limited to only one element that bears radially inward on the tubing. Indeed a resilient wall portion of an otherwise rigidly defined passage that can be deflected under the influence of the compression device to close the passage can be employed in place of the resilient tube.

Also, the embodiments described use either right-handed or left-handed threads to join the distal and proximal body members of the closure device and cause slight axial movement as the compression member moves in opening or closing the tube. The means of joinder and movement between the distal and proximal body members could also be found in other rotatable connections to give the same type of operation, some in which there is no axial advance at all, so the closure device, in certain aspects, is not limited to threaded surfaces for joining the component members.

For the syringe-actuated aspect of the invention, to obtain some of the advantages, it is possible to employ other two-part rotary valve constructions, such as two relatively rotatable disks each having an aperture which through rotation of the disks line up to define the passage and through opposite rotation move out of alignment to close the passage.

It will be understood the foregoing disclosure and description of the invention and alternative constructions are illustrative and explanatory thereof, and various changes in the size, shape and materials, as well as in the details of the illustrated constructions may be made without departing from the spirit of the invention.

We claim:

1. A catheter introducer kit comprising in combination a catheter introducer sheath assembly and a catheter containing a vena-cava filter and a stabilizer for placement of said filter, said catheter introducer sheath assembly comprising the combination of an elongated, flexible introducer sheath defining a passage and a closure device having a through passage extending between proximal and distal ends, said introducer sheath joined to the distal end of said closure device, the passages through said sheath and said closure device having a diameter sufficient to pass said catheter therethrough, said closure device comprising the combination of a resilient member at least partially defining said throughpassage of said closure device, said throughpassage having an axis;

a body including first and second relatively rotatable body portions, said first body portion being stationary with respect to said resilient member and said second body portion including an internal cam having a cam surface oriented about and spaced from the axis of said throughpassage with a first surface portion disposed relatively closer to said axis than a circumferentially spaced second surface portion; and a compression member positioned in a radially extending aperture in said first body portion and biased radially outward by said resilient member to maintain contact with said cam surface, said members of said combination of said closure device cooperatively related to enable adjustment of the radial compression of said resilient member for closing or opening said passage by relative rotation of said second body portion with respect to said first body portion to position, in dependent manner, said compression member radially closer to or further from said axis to close or open said throughpassage or to engage, with desired tightness, the said catheter or a guidewire extending or sliding through said closure device and sheath.

2. The kit of claim 1 wherein said passages through said closure device and said attached sheath are sized to pass a catheter containing a vena cava filter and a stabilizer wire for placement of the filter.

3. The kit of claim 2 wherein said passages are of the order of ⅜ inch diameter.

4. The kit of claim 1, 2 or 3 wherein said compression member is adjustable by manual manipulation of said second body portion to selected intermediate rotatable positions relative to said first body portion to cause said resilient member to lightly engage the sides of said catheter being inserted through said catheter introducer sheath assembly to impede outward blood flow along the sides of said catheter while permitting slidable insertion thereof.

5. The kit of claim 1 in combination with a removable elongated dilator disposed in said sheath, said dilator having a tapered distal portion extending distally beyond the sheath.

6. The kit of claim 5 wherein said dilator has a small axial passage enabling said dilator, sheath and closure device to be slid over a pre-placed guidewire for guiding the sheath into a predetermined position.

7. The catheter introducer kit of claim 1 including a dilator, said dilator having a small axial passage enabling said dilator, sheth and closure device to be slid over a pre-placed guidewire for guiding the sheath into a predetermined position.

8. A catheter introducer sheath assembly comprising the combination of an elongated, flexible introducer sheath defining a passage and a closure device having a through passage extending between proximal and distal ends, said introducer sheath joined to the distal end of said closure device, the passage through said sheath and the throughpassage through said closure device having diameters sufficient to pass a respective catheter therethrough, said closure device comprising the combination of a resilient member at least partially defining said throughpassage of said closure device, said throughpassage having an axis;

a body including first and second relatively rotatable body portions, said first body portion being stationary with respect to said resilient member and said second body portion including an internal cam having a cam surface oriented about and spaced from the axis of said throughpassage with a first surface portion disposed relatively closer to said axis than a circumferentially spaced second surface portion: and a compression member positioned in a radially extending aperture in said first body portion and biased radially outward by said resilient member to maintain contact with said cam surface, said members of said combination of said closure device cooperatively related to enable adjustment of the radial compression of said resilient member for closing or opening said throughpassage by relative rotation of said second body portion with respect to said first body portion to position, in dependent manner, said compression member radially closer to or further from said axis to close or open said throughpassage or to engage, with desired tightness, a catheter or guidewire extending or sliding through said closure device and sheath and wherein said cam defines a smooth spiral-form surface.

9. The device of claim 8 wherein a stop surface is defined at the end of said second cam surface portion arranged to engage said compression member and stop relative motion apart of said body portions when said compression member reaches a passage-opening position and said first and second body portions are further constructed to engage each other and stop threaded-together motion when said compression member reaches a passage-closing position.

10. The device of claim 9 wherein said first surface portion of said cam positions said compression member radially to completely close in fluid-tight manner said throughpassage and said second surface portion positions said compression member to fully open said throughpassage for fluid flow.

11. The device of claim 1 or 8 wherein said compression member is a single ball-form member.

12. The device of claim 1 or 8 wherein said second rotatable body portion includes a first stop member which is engaged by said compression member and prevents disassembly of said body portions by blocking further relative rotation of said body portions.

13. The device of claim 1 or 8 wherein the closure device further includes a side channel distal of the axial position of the compression member.

14. The device of claim 1 or 8 wherein said second rotatable body portion has an external surface exposed for engagement and rotatable operation by the hand of a user.

15. The device of claim 8 wherein said first body portion fixes the position of said resilient member and a second body portion, carrying said cam surface, is mounted to rotate upon said first body portion.

16. The device of claim 8 where said resilient member comprises a section of tubing comprised of silicone elastomer.

17. The device of claim 8 wherein said second rotatable body portion is axially and rotatably positioned by a screw thread.

18. The device of claim 8 wherein said compression member is held axially fixed, relative to said resilient member.

19. The device of claim 8 wherein a stationary body portion holds said resilient member in fixed relation and defines a radially extending aperture in which said compression member is axially confined, and permitted to move radially against said resilient member.

20. The device of claim 8 wherein said resilient member comprises a tubing member compressed axially and confined radially for sealing engagement of surfaces at its proximal and distal ends.

21. The device of claim 8 constructed so that said rotation of said second body portion to open and close said throughpassage is substantially one-half turn.

22. The device of claim 8 wherein said resilient member and the part of any body portion that overlies said resilient member comprise clear plastic material enabling visual examination of flow through said throughpassage.

23. The device of claim 8 wherein said first and second body portions are formed of moldable material.

* * * * *

UNITED STATES PATENT AND TRADEMARK OFFICE
CERTIFICATE OF CORRECTION

PATENT NO. : 5,397,310
DATED : March 14, 1995
INVENTOR(S) : Michael S.H. Chu et al.

It is certified that error appears in the above-indentified patent and that said Letters Patent is hereby corrected as shown below:

Col. 1, line 27, "stopcoak" should be --stopcock--.

Col. 3, line 66, "8A and 8D" should be --8A-8B--.

Col. 5, line 20, "128" should be --.128--.

Col. 12, line 4, "or a to a syringe" should be --or to a syringe--.

Col. 13, claim 1, lines 14, 21, and 37 "throughpassage" should be --through passage--.

Col. 13, claim 3, line 46 "5/8" should be --1/8--.

Col. 13, claim 7, line 66, "sheth" should be --sheath--.

UNITED STATES PATENT AND TRADEMARK OFFICE
CERTIFICATE OF CORRECTION

PATENT NO. : 5,397,310
DATED : March 14, 1995
INVENTOR(S) : Michael S.H. Chu et al.

It is certified that error appears in the above-indentified patent and that said Letters Patent is hereby corrected as shown below:

Col. 14, claim 8, lines 7, 12, 13, 19 and 35 "throughpassage" should be --through passage--.

Col. 14, claim 10, lines 52 and 54 "throughpassage" should be --through passage--.

Col. 16, claim 21, line 9 "throughpassage" should be --through passage--.

Signed and Sealed this

Second Day of April, 1996

Attest:

BRUCE LEHMAN

Attesting Officer    Commissioner of Patents and Trademarks